United States Patent
Chauhan et al.

(10) Patent No.: US 12,090,273 B1
(45) Date of Patent: Sep. 17, 2024

(54) SYSTEM AND METHOD FOR AUTOMATED INTUBATION

(71) Applicant: Someone is Me, Dallas, TX (US)

(72) Inventors: Sanket Singh Chauhan, Dallas, TX (US); Aditya Narayan Das, Dallas, TX (US)

(*) Notice: Subject to any disclaimer, the term of this patent is extended or adjusted under 35 U.S.C. 154(b) by 869 days.

(21) Appl. No.: 17/121,709

(22) Filed: Dec. 14, 2020

Related U.S. Application Data

(60) Provisional application No. 62/947,809, filed on Dec. 13, 2019.

(51) Int. Cl.
| | | |
|---|---|---|
| *A61M 16/04* | (2006.01) | |
| *G06F 18/214* | (2023.01) | |
| *G06N 3/08* | (2023.01) | |
| *G06V 20/40* | (2022.01) | |

(52) U.S. Cl.
CPC ....... *A61M 16/0488* (2013.01); *G06F 18/214* (2023.01); *G06N 3/08* (2013.01); *G06V 20/49* (2022.01); *A61M 2205/3306* (2013.01); *A61M 2205/502* (2013.01)

(58) Field of Classification Search
CPC .......... A61M 16/0003; A61M 16/0402; A61M 16/0418; A61M 16/0427; A61M 16/0461; A61M 16/0463; A61M 16/0465; A61M 16/0488; A61M 16/04–0497; A62M 16/021–026
USPC .................................................... 128/200.26
See application file for complete search history.

(56) References Cited

U.S. PATENT DOCUMENTS

| | | | | |
|---|---|---|---|---|
| 2011/0301447 | A1* | 12/2011 | Park ................ | G06T 7/0016 600/407 |
| 2015/0059736 | A1* | 3/2015 | Qiu ................. | G06F 18/2193 128/200.26 |
| 2018/0296281 | A1* | 10/2018 | Yeung ............. | A61B 34/32 |
| 2019/0380781 | A1* | 12/2019 | Tsai ............... | A61B 5/067 |
| 2020/0375433 | A1* | 12/2020 | Polosky .......... | A61B 1/00149 |
| 2021/0034841 | A1* | 2/2021 | Segal .............. | G06N 3/088 |
| 2022/0257889 | A1* | 8/2022 | Alonso Babarro | A61B 1/01 |

* cited by examiner

*Primary Examiner* — Valerie L Woodward
*Assistant Examiner* — Paige Kathleen Bugg

(57) ABSTRACT

A system, method and apparatus to automatically perform endotracheal intubation in a patient comprising, inserting a blade inside the upper airway of the patient to retract an anatomical structure; inserting a bending portion and a tube arranged on the bending portion inside the airway of the patient; collecting airway data using at least one imaging sensor arranged on the bending portion; communicating collected airway data to a processing circuitry; predicting an intended path for insertion of the tube and generating control signals using the processing circuitry, wherein the intended path is predicted based on at least one anatomical structure recognized by the processing circuitry using the collected airway data; displaying an intended path via a user interface to display at least one intended path to an operator and also allow the operator to select an intended path; and communicating the control signals generated by the processing circuitry to at least one actuation unit to actuate the three-dimensional movement of the tube.

18 Claims, 9 Drawing Sheets

SYSTEM AND METHOD FOR AUTOMATED INTUBATION

BACKGROUND

The present invention relates to an automated system and method to insert an invasive medical device inside a patient, and more particularly to an automated system and method to insert an invasive medical device inside a cavity of a patient using image-based guidance.

This section describes the technical field in detail and discusses problems encountered in the technical field. Therefore, statements in the section are not to be construed as prior art.

Efficient implantation of medical devices inside a patient's body is one of the utmost need felt by the medical community nowadays. One reason for the arising need is the vast arena of applications provided by invasive medical devices, ranging from insertion of pacemakers in the chest ensuring the heart beats at an appropriate rate, to insertion of urinary catheters. Another reason is the large number of complications and intricacies that come across medical operators, physicians, and anesthesiologists during the implantation procedures, which demands an immediate turn around to prevent morbidity and mortality.

One such application of implantation of invasive devices is endotracheal intubation which is done to keep the airway of a patient open to support breathing. Endotracheal intubation (or ETI) is carried out by using a laryngoscope to visualize the glottis opening and then inserting a tube through it. The physician can see the glottis directly through their eyes after manipulating the anatomical structures in the upper airway with the laryngoscope creating a "straight line of vision". The clear visualization of the glottis opening using a laryngoscope depends on several factors like facial structure, mallampati score, dental conditions, and joint rigidity. Hence, endotracheal intubation is a process that requires a lot of skill and training. Even with appropriate training, it may be difficult to visualize the glottis opening and insert a tube.

It is estimated that during pre-hospital care, about 81% of endotracheal intubations are performed by non-physicians and 19% of them are performed by physicians. The unpredictable environment during prehospital care further adds to the complexity of successful intubation. It is estimated that the first attempt failure rate while doing endotracheal intubation is as high as 41%. This delay in intubating a patient has severe consequences. The hypoxia can lead to permanent brain damage within 4 minutes and death within 10 minutes.

Alternate methods of intubation using a video laryngoscope provide a much better view as they contain the camera at the tip of the scope and hence, the "straight line of vision" is not needed. The camera projects the image on a monitor and looking at the monitor, the endotracheal tube can be manually inserted by the physician. This still needs a lot of manual dexterity and visual-spatial cognition. These are also difficult skills to learn. The first attempt failure rates using video laryngoscopes can also be high.

When the patient cannot be intubated, several alternate methods are tried including supraglottic ventilation devices, special airway devices such as King's tube or Combitube, mask ventilation, and in some cases, even an emergency cricothyroidotomy—which means putting an incision in the neck and trachea, and inserting a tube through that opening. As expected, these procedures are not as effective as simple endotracheal intubation and maybe a lot more invasive to the patient with long-term sequelae.

Most of the guided intubation systems and methods in state of the art have limitations which lead to issues such as higher delays and failure rates during intubation. Hence there is a definite need to design a system and method which can not only assist in fast and successful intubations but can also work with complete autonomy and minimal operator (or user) intervention. Operator and user can be used interchangeably.

Patients who are severely affected with severe respiratory infections such as the COVID-19 virus may develop respiratory distress which requires intubation and ventilation. Since the healthcare provider is very close to the infected patient and is in direct contact with the saliva of such patients, they are at risk of contracting this disease themselves while following the standard of care for such patients. Furthermore, the disease transmission to healthcare providers is directly related to, among other things, the duration and extent of contact with the patient, making ETI high-risk procedures for transmission of the infection.

The present invention has an object, among others, to overcome deficiencies in the prior art such as noted above.

SUMMARY

References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

In an aspect of the present invention, an automated system inserts an invasive medical device inside a cavity of a patient. The automated system includes a processing circuitry that receives data from at least one data source to recognize structures relevant to the cavity of the patient and predict an intended path for insertion of the invasive medical device inside the patient. The processing circuitry further generates and communicates the control signals to at least one actuation unit based on the intended path, to actuate the three-dimensional movement of the invasive medical device.

The processing circuitry can utilize machine learning models along with the data received from the data source(s) to recognize structures relevant to the cavity of the patient, predict an intended path, generate and communicate control signals to the actuation unit to actuate the three-dimensional movement of the invasive medical device. The intended path will be the path along which the device will guide the invasive medical device once movement has commenced. The generation of the machine learning model involves receiving or collecting training data in the form of predetermined datasets to train at least one neural network. A form of this neural network could be an edge-implemented deep neural net-based object detector which is well known in the art Other forms of machine learning other than neural networks can be substituted, as would be well known to a person of skill in the art. The predetermined datasets can be, but are not limited to, images and videos.

The data source(s) can be an imaging sensor. These sensors can include but are not limited to cameras, infrared cameras, sonic sensors, microwave sensors, photodetectors, or others known to the person skilled in the art can also be employed to achieve the same purpose. The data received from the imaging sensor can be displayed on a user interface to provide a view of the cavity of the patient to an operator. Additionally, the intended path and the recognized structures can be overlaid over the data received from the imaging sensor on the user interface for effective visual guidance to the operator.

In an exemplary embodiment of the present invention, an automated intubation system predicts the intended path for insertion of a tube and generates control signals for at least one actuation unit. The intended path is predicted based on at least one anatomical structure recognized using the data received from at least one imaging sensor. An overlay of intended path and/or recognized anatomical structures is also displayed on a user interface over the data received by the user interface from the imaging sensor(s), for effective visual guidance during intubation. The intended path displayed on the user interface is also adjustable by the operator and/or overridden by the operator if the operator is not satisfied with the intended path of insertion. The operator can then select the suggested or adjusted intended path for the system to follow during the intubation process.

Additionally, the overlaying of the intended path can also be visualized on the user interface in the form of augmented reality and/or any other form which provides effective visual guidance to the operator.

In one preferred embodiment, the automated intubation system comprises a main body, a bending portion, a flexible part that connects the main body with the bending portion, a housing unit arranged on the bending portion comprising of at least one imaging sensor, a tube for intubation arranged on the flexible part and the bending portion, a circuitry, a user interface, a disposable and/or reusable sleeve having a blade at one end to retract anatomical structures and at least one actuation unit to actuate the three-dimensional movement of the tube. The length of the bending unit is variable and can only be at the tip of the flexible part, or can cover the flexible part completely. In other embodiments, the bending portion can be located within any portion of the flexible part, determined by several factors, including but not limited to, the relevant uses and anatomical structures that need to be navigated. Preferably, the disposable and/or reusable sleeve is removably coupled to the main body. The imaging sensor(s) is preferably a camera, although sensors such as infrared, photodetectors, or other feasible means known to the person skilled in the art can be employed to achieve the same purpose.

In a preferred embodiment of the present invention, the circuitry, the user interface, and the actuation unit is a part of the main body. The circuitry further comprises a processing circuitry, a power circuitry, and a communication circuitry.

In an alternative embodiment of the present invention, the circuitry and the user interface are arranged separately from the main body within at least one separate box.

The processing circuitry is utilized to both predict the intended path for insertion of the tube-based on at least one recognized anatomical structure and to generate control signals. The processing circuitry is also utilized to recognize anatomical structure using the data received from the imaging sensor and at least one pre-trained machine learning model. The actuation unit receives control signals from the processing circuitry to actuate the three-dimensional movement of the tube. The actuation unit particularly uses connections with the bending portion to actuate the bending movement of the tube in X and Y planes. The actuation unit also comprises a sliding mechanism to actuate the sliding movement of the tube in Z plane by moving the bending portion and its associated actuation unit on a rail track. Alternatively, the sliding mechanism actuates the sliding movement of the tube in Z plane by direct contact or abutment with the tube without displacing the bending portion and its associated actuation unit. A person of skill in the art also realized that other three-dimensional coordinate schemes such as radial, polar, cylindrical, and spherical can be used in substitution of the x, y, and z coordinates described herein.

In another embodiment of the present invention, the processing circuitry is only used to predict the intended path and generate control signals, while recognition of anatomical structures using imaging sensor data and machine learning model is performed by an separate independent processing circuitry.

The machine learning model is a part of a computer vision software developed by training one or more neural networks over a labeled dataset of images, where the labeled dataset of images is built by converting a collection of intubation procedure videos into image files and labeling anatomical structures on the image files. In an alternative embodiment, the machine learning model generation involves receiving or collecting training data in form of predetermined datasets to train at least one neural network. The predetermined datasets can be but are not limited to images, audios, and videos recorded and collected during the procedure.

In another embodiment of the present invention, the control signals received by the actuation unit to actuate three-dimensional movement of the tube are generated manually by a pair of up and down buttons arranged on the outer surface of the main body or touch buttons arranged on the user interface. Hence, the system provides a manual mode of actuation if required by an operator. The pair of up and down buttons and touch buttons can also be used by the operator to override the automated actuation of the tube if the operator is not satisfied with the intended path.

In another aspect of the present invention, a method to automatically insert an invasive medical device inside the cavity of the patient is provided which comprises inserting a bending portion and an invasive medical device arranged on the bending portion inside the cavity of the patient. The method includes collecting airway data using an imaging sensor arranged on the bending portion and communicating the collected airway data to a processing circuitry to predict an intended path of insertion of the invasive medical device and generate control signals. The control signals are then communicated to at least one actuation unit to actuate the three-dimensional movement of the invasive medical device. The intended path is preferably predicted by the processing circuitry based on the recognition of at least one structure relevant to the cavity using the data communicated from the imaging sensor.

Additionally, the prediction of the intended path of insertion and recognition of structure relevant to the cavity can be performed by the processing circuitry by utilizing a machine learning model along with data communicated from the imaging sensor. The generation of the machine learning model involves receiving or collecting training data in the form of predetermined datasets to train at least one neural network. The predetermined datasets can be but are not limited to images and videos. It is foreseeable that the device disclosed in this patent can be utilized in different cavities other than the breathway described herein or to perform different tasks within any of those body cavities.

In an exemplary embodiment of the present invention, a method to automatically intubate the patient by inserting a bending portion and a tube arranged on the bending portion inside an airway of the patient is provided. The method further includes collecting airway data using an imaging sensor arranged on the bending portion and communicating the collected airway data to a processing circuitry to predict an intended path of insertion of the tube and generate control signals for actuating the three-dimensional movement of the tube. The intended path is preferably predicted by the processing circuitry based on the recognition of at least one anatomical structure using the data communicated from the imaging sensor. The processing circuitry utilizes a machine learning model and the data communicated from the imaging sensor to recognize anatomical structures and predict the intended path of insertion of the tube.

The method can also involve displaying airway data on a user interface to highlight a view of the airway to an operator. Additionally, it involves overlaying of an intended path and recognized anatomical structures on a user interface over the data communicated from the imaging sensor for effective visual guidance to an operator.

There are advantages of having a semi-automated invasive device insertion system as compared to a fully automated system. The commercialization of such a system will need regulatory approval from a government agency such as the FDA and the pathways for a semi-automated system could be simpler and less complex. Additionally, having a fully automated system can potentially create a layer of legal liabilities to which the company may be vulnerable. Furthermore, as good as the technology might be, it is good for a trained professional to supervise the procedure and if necessary manually override it to ensure correct intubation. The technical hurdles in developing and producing a deployable system may be reduced when comparing the semi-automated system to a fully automated system. Finally, having in-built verification and control mechanisms and usability layers that enforce the correct path will prevent injuries and are safer for the patient.

In alternative embodiments, complementary sensors can be integrated with the device that can provide real-time information regarding relevant clinical parameters of the patient such as vital signs, including but not limited to pulse and heart rate, respiratory rate, oxygen saturation levels, temperature, blood pressure; and other laboratory results, but not limited to blood gas levels, glucose levels, and other results that a person trained in the state of art will know.

In other embodiments, an operator can connect to the device remotely over the internet and can operate the device using a similar user interface.

Other embodiments and preferred features of the invention, together with corresponding advantages, will be apparent from the following description and claims.

BRIEF DESCRIPTION OF THE DRAWINGS

Various aspects as well as embodiments of the present invention are better understood by referring to the following detailed description. To better understand the invention, the detailed description should be read in conjunction with the drawings.

DETAILED DESCRIPTION

Figure 1:
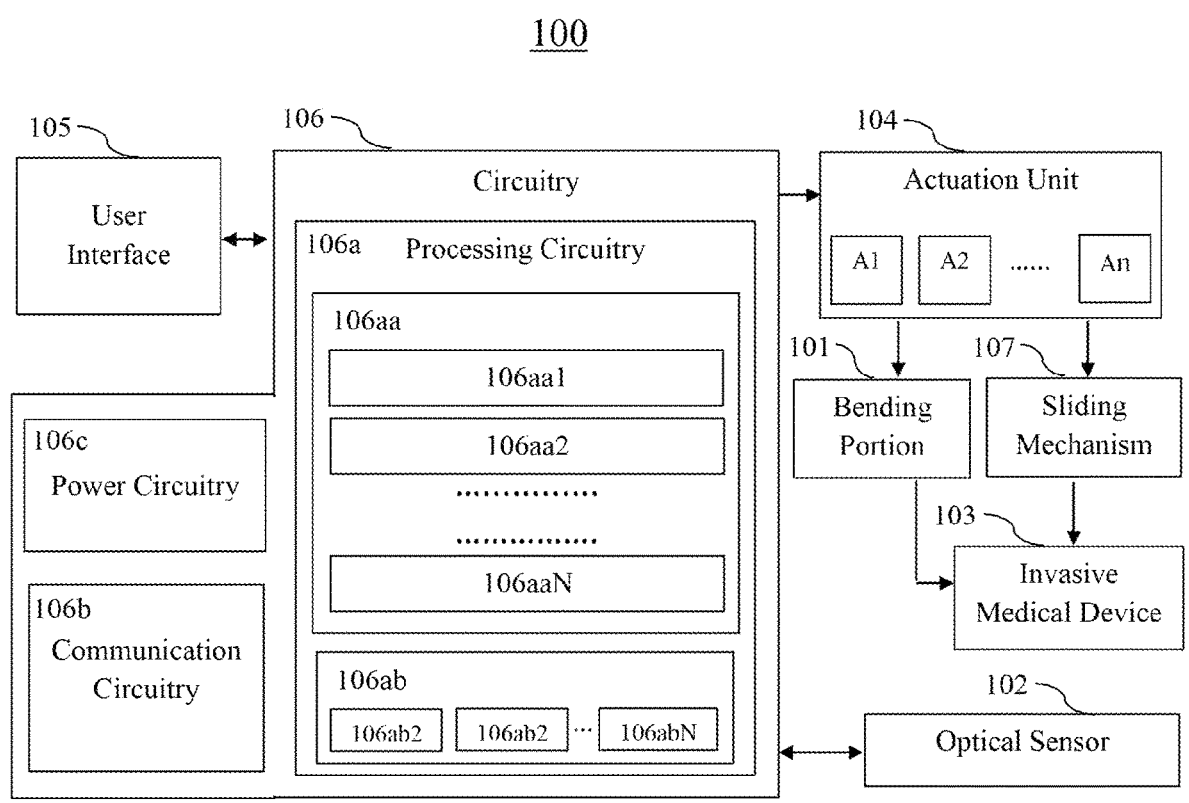
FIG. 1 illustrates an exemplary architecture of the automated system to insert an invasive medical device inside a patient according to the present invention.

The present disclosure is best understood with reference to the detailed figures and description set forth herein. Various embodiments have been discussed with reference to the figures. However, a person skilled in the art will readily appreciate that the detailed descriptions provided herein with respect to the figures are merely for explanatory purposes, as the methods and system may extend beyond the described embodiments. For instance, the teachings presented, and the needs of a particular application may yield multiple alternatives and suitable approaches to implement the functionality of any detail described herein. Therefore, any approach may extend beyond certain implementation choices in the following embodiments.

Methods of the present invention may be implemented by performing or executing manually, automatically, or a combination thereof, of selected steps or tasks. The term "method" refers to manners, means, techniques, and procedures for accomplishing a given task including, but not limited to, those manners, means, techniques, and procedures either known to or readily developed from known manners, means, techniques, and procedures by practitioners of the art to which the invention belongs. The descriptions, examples, methods, and materials presented in the claims and the specification are not to be construed as limiting but rather as illustrative only. Those skilled in the art will envision many other possible variations within the scope of the technology described herein.

While reading a description of the exemplary embodiment of the best mode of the invention, hereinafter referred to as "exemplary embodiment"), one should consider the exemplary embodiment as the best mode for practicing the invention at the time of filing of the patent in accordance with the inventor's belief. As a person with ordinary skills in the art may recognize substantially equivalent structures or substantially equivalent acts to achieve the same results in the same manner, or in a dissimilar manner, the exemplary embodiment should not be interpreted as limiting the invention to one embodiment.

The discussion of a species (or a specific item) invokes the genus (the class of items) to which the species belongs as well as related species in this genus. Similarly, the recitation of a genus invokes the species known in the art. Furthermore, as technology develops, numerous additional alternatives to achieve an aspect of the invention may arise. Such advances are incorporated within their respective genus and should be recognized as being functionally equivalent or structurally equivalent to the aspect shown or described.

Unless explicitly stated otherwise, conjunctive words (such as "or", "and", "including" or "comprising") should be interpreted in the inclusive, and not the exclusive sense.

As will be understood by those of the ordinary skill in the art, various structures and devices are depicted in the block diagram to not obscure the invention. It should be noted in the following discussion that acts with similar names are performed in similar manners unless otherwise stated.

The foregoing discussions and definitions are provided for clarification purposes and are not limiting. Words and phrases are to be accorded their ordinary, plain meaning unless indicated otherwise The invention can be understood better by examining the figures, wherein FIG. 1 is an illustration of an exemplary architecture of an automated system 100 to insert an invasive medical device inside a cavity of a patient. The system comprises a bending portion 101, an imaging sensor 102, an invasive medical device 103, at least one actuation unit 104, a user interface 105, and a circuitry 106. The circuitry further comprises a processing circuitry 106a to generate control signals based on the inputs from at least one imaging sensor and machine learning model, a communication circuitry 106b to provide data/signal communication between different components of the system, and a power circuitry 106c. The actuation unit contains a sliding mechanism 107 to provide movement to the invasive medical device in the Z plane.

The processing circuitry 106a can be a single processor, logical circuit, a dedicated controller performing all the functions, or a combination of process assisting units depending upon the functional requirement of the system. In an exemplary embodiment, the processing circuitry comprises two independent process assisting units 106aa and 106ab. The process assisting unit 106aa is computer vision software utilizing machine learning techniques and data received from the imaging sensor 102 to perform at least one function (106aa1, 106aa2 . . . 106aaN) for automating the process of intubation. The functions include recognition of structure around and inside the cavity of the patient and prediction of an intended path for insertion of the invasive medical device 103 inside the patient. Alternatively, the processing circuitry 106aa predicts the intended path based on the input from an imaging sensor, remotely received sample historical data from the actuation unit of multiple devices, or a machine learning model. The system further stores the intended path for maintaining a log of the device operation for regulatory purposes in the memory (not shown in the system). The logs of the device can be shared with a remote device for monitoring and controlling purposes. Further information can be stored or shared such as the imagery from the one or more imaging sensors as well as state and decision points that may be shared with remote servers to further improve the machine learning model or for other purposes such as regulatory or training purposes. This information can be stored locally on the device or on remote storage such as a server or on the cloud. The process assisting unit 106ab generates control signals based on the intended path predicted by process assisting unit 106aa. The control signals generated by the process assisting unit 106ab are then communicated from the processing circuitry to the actuation unit 104 via the communication circuitry 106b, based upon which the actuation unit actuates at least one of the bending portion 101 and the sliding mechanism 107 to provide the three-dimensional movement to the invasive medical device. The process assisting units 106ab can also be an integrated part of the actuation unit 104 and the control signals can be received by the actuation unit 104 through wireless or wired communication circuitry. The processing circuitry 106aa can also be remotely connected through a network or wireless media with the actuation unit 104 to send the control signals. The communication circuitry can also be an integrated part of the actuation unit. Each of the functions described above may be combined with another function within a single functional unit, for each and all of the functions described above.

The communication circuitry 106b can also be distributed in the complete system to act as an element of two-way data/signal transfer. The communication circuitry can be wired or wireless. The power circuitry 106c distributes power to all the units of the system. The power circuitry includes a rechargeable battery or a direct regulated power supply.

The actuation unit 104 can be a rotational motor, linear motor, and/or a combination of both rotational and linear motor. In an exemplary embodiment, multiple actuation units (A1, A2 . . . . An) independently actuate the bending portion 101 and sliding mechanism 107 to provide three-dimensional movement. Alternatively, the bending portion 101 and the sliding mechanism 107 may also be actuated in integration with each other using a single actuation unit. The system can track the movement of the invasive medical device and compare it with the intended path to compute deviation and calibrate the movement. The calibration can be done automatically or through manual intervention. The data of actual movement can be sent to a remote device for monitoring purposes.

The user interface 105 is in two-way communication with the processing circuitry 106a. The user interface is preferably a display device to display data received from the imaging sensor 102 and an overlay of the recognized structure and/or the intended path from the processing circuitry over the data received from the imaging sensor to assist an operator in effective visual guidance. Alternatively, a user interface can be any device that can enable the operator's interaction with the automated system such as an audio input/output, gesture-enabled input, augmented reality enabled system, and/or a projection device. The user interface can also be a head-up display or head-mounted display to support virtual reality form of interaction. The user interface 105 can be used to select the suggested intended path or to override the suggested path and to select a modified intended path created by the operator by modifying the suggested intended path.

Figure 2:
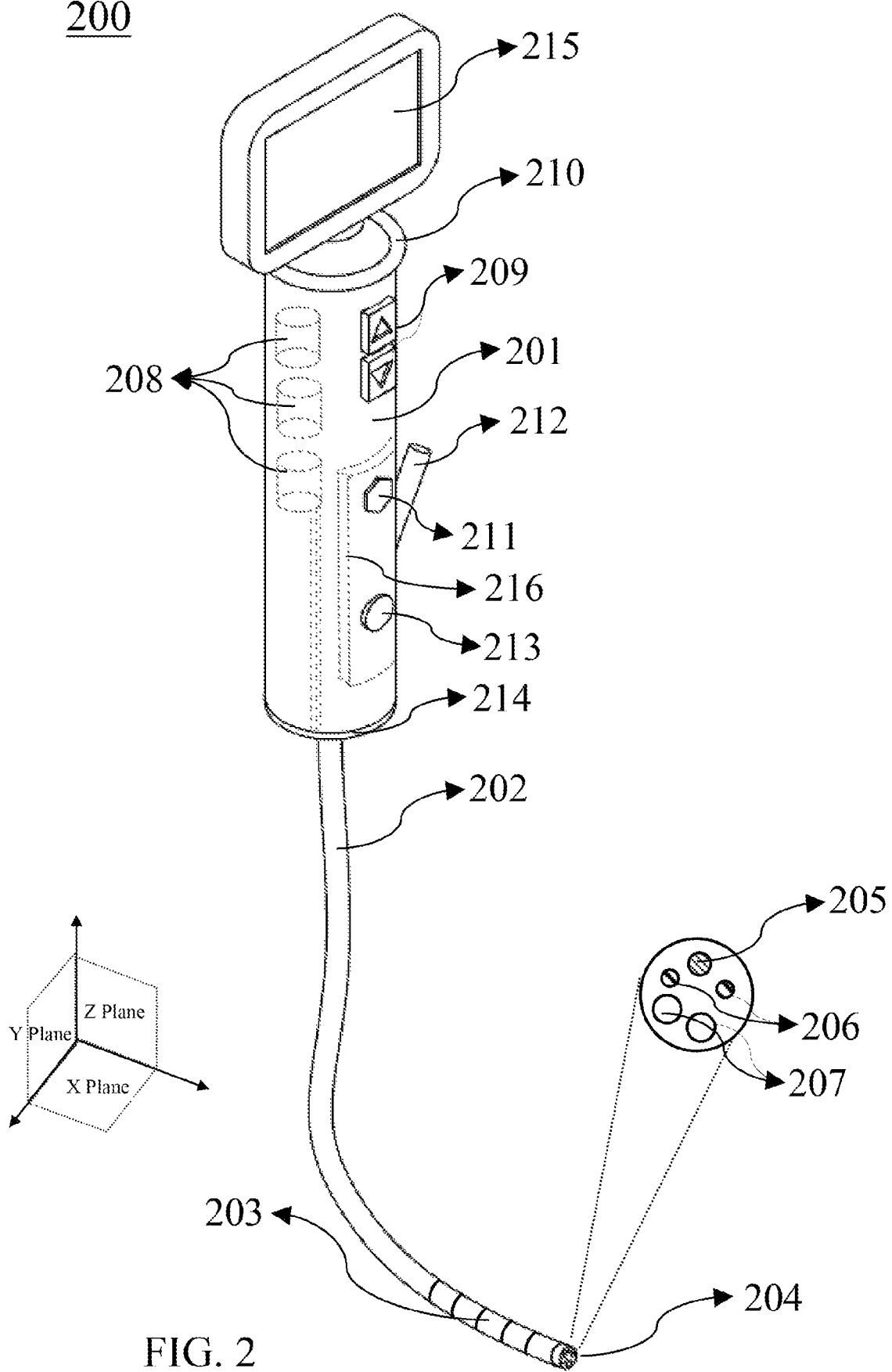
FIG. 2 illustrates an exemplary embodiment of the automated intubation system according to the present invention.

FIG. 2 is an illustration of an exemplary embodiment of the automated intubation system 200, which comprises a main body 201, a flexible part 202 to connect the main body to a bending portion 203, a housing unit 204 attached to the bending portion. The housing unit further supports at least one imaging sensor 205, at least one guide light 206, and at least one outlet channel 207. Preferably the imaging sensor is a wide CMOS camera and the guide light is a LED light that is automatically turned on when the system is turned on. Alternatively, an independent control switch of the guide light and the imaging sensor can also be provided.

The main body further comprises at least one actuation unit 208 to translate control signal received from the processing circuitry into a three-dimensional movement for advancing tube(s) in the patient cavity. The actuation unit 208 can be a rotational motor, linear motor, and/or a combination of both rotational and linear motor. Optionally, the outer surface of the main body 201 has at least one button or knob 209 to manually control the actuation, a light source 210 to indicate the power status of the automated system 200, a switch 211 to turn on or off the automated system, at least one port 212 for suction and a tube release switch or lever 213 to disconnect the tube from the main body.

In one embodiment, the actuation unit 208 further comprises a sliding mechanism 214. The sliding mechanism can either be an integral part of the actuation unit or a separate unit connected to the actuation unit. The sliding mechanism can be a moveable base plate connected to the actuation unit via a rack and pinion mechanism (not shown), where the pinion is connected to the actuation unit for rotational motion, and the rack is connected to the moveable base plate for the conversion of rotational motion into vertical motion and/or displacement. A person of skill in the art will be knowledgeable of other methods or mechanisms, to connect the actuation unit to the moveable base plate, to achieve the same sliding mechanism. The primary purpose of the sliding mechanism is to provide Z plane movement to the tube. The use of a sliding mechanism activation unit 208 is not required by this disclosure, as disclosed below, a number of electromechanical systems can be used to provide movement in the Z plane for the intrusive medical device.

Alternatively, the two independent actuation units can be used to actuate the bending portion 203 and sliding mechanism 214. The processing circuitry (shown in FIG. 1) can send control signals of X and Y plane movement to the actuation unit controlling the movement of the bending portion and Z plane movement to the actuation unit associated with the sliding mechanism.

Alternatively, there are a number of different arrangements of the actuation units for the movement of the tube in three dimensions that would be readily apparent to a person of skill in the art. These can include the use of rotational, geared, coiled, or screw based activation units as well as free-floating actuation units. Due care must be given to allow for accuracy in movement in the X and Y planes as well as the magnitude of movement required in the Z plane.

A user interface 215 is also attached to the main body 201 to display data received from the imaging sensor 205. Preferably, the user interface is a display device attached to the main body. Alternatively, the user interface is a touch-enabled display device comprising at least one button to trigger actuation, a button to release the tube, and a power button (not shown). A user interface can be any device that can enable the operator's interaction with an automated system such as an audio input, audio output, or gesture-enabled input. In another embodiment, the user interface can be comprised of an intelligent agent that provides the necessary operator feedback.

The main body 201 also comprises a circuitry 216, which further comprises a processing circuitry, a communication circuitry, a power circuitry.

The bending portion 203 is connected to the actuation unit 208. Preferably, the bending portion 203 is connected to the actuation unit 208 via at least one cord (not shown in FIG. 2). The cord(s) is connected to the actuation unit and passes through the flexible part to reach and connect to the bending portion to actuate the bending motion and/or movement of the bending portion. Alternatively, the cord(s) can be replaced by any feasible mechanical link such as a thread, wire, cable, and chain. A person of skill in the art will be knowledgeable of other methods or means, to connect the actuation unit to the bending portion, to provide two-dimensional movement in X and Y plane to the bending portion 203.

Figure 3:
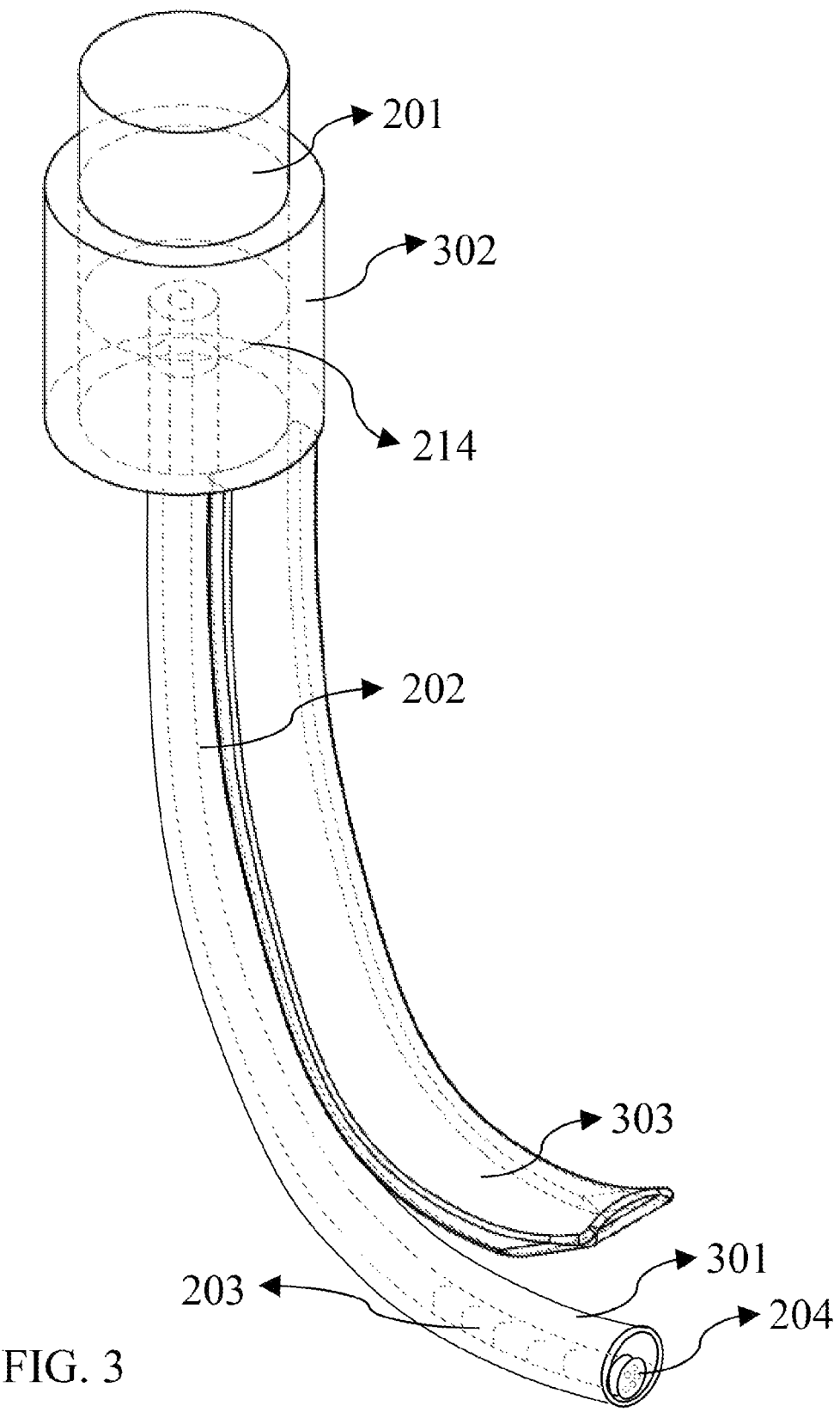
FIG. 3 illustrates an assembly of a main body, disposable sleeve, and the tube of the automated intubation system according to the present invention.

FIG. 3 is an illustration of an assembly of the main body 201 with a tube 301 and a sleeve 302 of the automated intubation system 200. The tube can be arranged longitudinally on the flexible part 202 and the bending portion 203. Alternatively, the tube can be partially arranged on the flexible part and partially arranged on the bending portion.

In general, the flexible part goes through the tube to provide a view of the respiratory tract via the imaging sensor(s) supported by the housing unit 204. The tube is but is not limited to an endotracheal tube which can include an oral, nasal, cuffed, uncuffed, preformed reinforced, double-lumen endobronchial tube or any custom tube.

The sleeve 302 can be s mechanically connected to the main body 201 to detachably connect a blade 303 with the main body preferably via a snug fit connection. Other feasible mechanical connections known to the person skilled in the art can also be employed to achieve the same purpose. The detachable blade 303 at one end of the sleeve 302 is provided to retract anatomical structures during the intubation procedure. The sleeve can be made of a disposable and/or a reusable material.

The blade 303 is designed to improve the efficacy of the blade for providing better visibility during the intubation process and can be shaped similar to the blades of conventional video laryngoscopes. The blade can additionally have an integrated pathway to guide the tube at an initial stage of intubation. The pathway can be an open tunnel through which the tube can pass through, or it can be formed at the blade using indents, railings, grooves, or a combination thereof.

The tube 301 can be in contact with the sliding mechanism 214 when arranged on the flexible part and the bending portion. The contact of the tube with the sliding mechanism enables displacement of the tube along the flexible part 202 and/or the bending portion 203 in Z plane when the actuation unit 208 actuates the sliding mechanism.

Alternatively, the sliding mechanism 208 displaces the bending portion 203 and the associated actuation unit in Z plane to insert and retract the bending portion inside the trachea of the patient. The actuation unit associated with the bending portion is particularly arranged on the rail guide (not shown) of the sliding mechanism, such that the actuation unit associated with the sliding mechanism can displace it accordingly.

The tube 301 is connected to the actuation unit 208 via its arrangement on at least one of the flexible part 202 and bending portion 203. The actuation unit actuates the bending portion to further actuate the bending motion of the tube in X and Y plane. In simple words, the bending portion acts as a guide for the tube to navigate the direction inside the airway of the patient.

Figure 4:
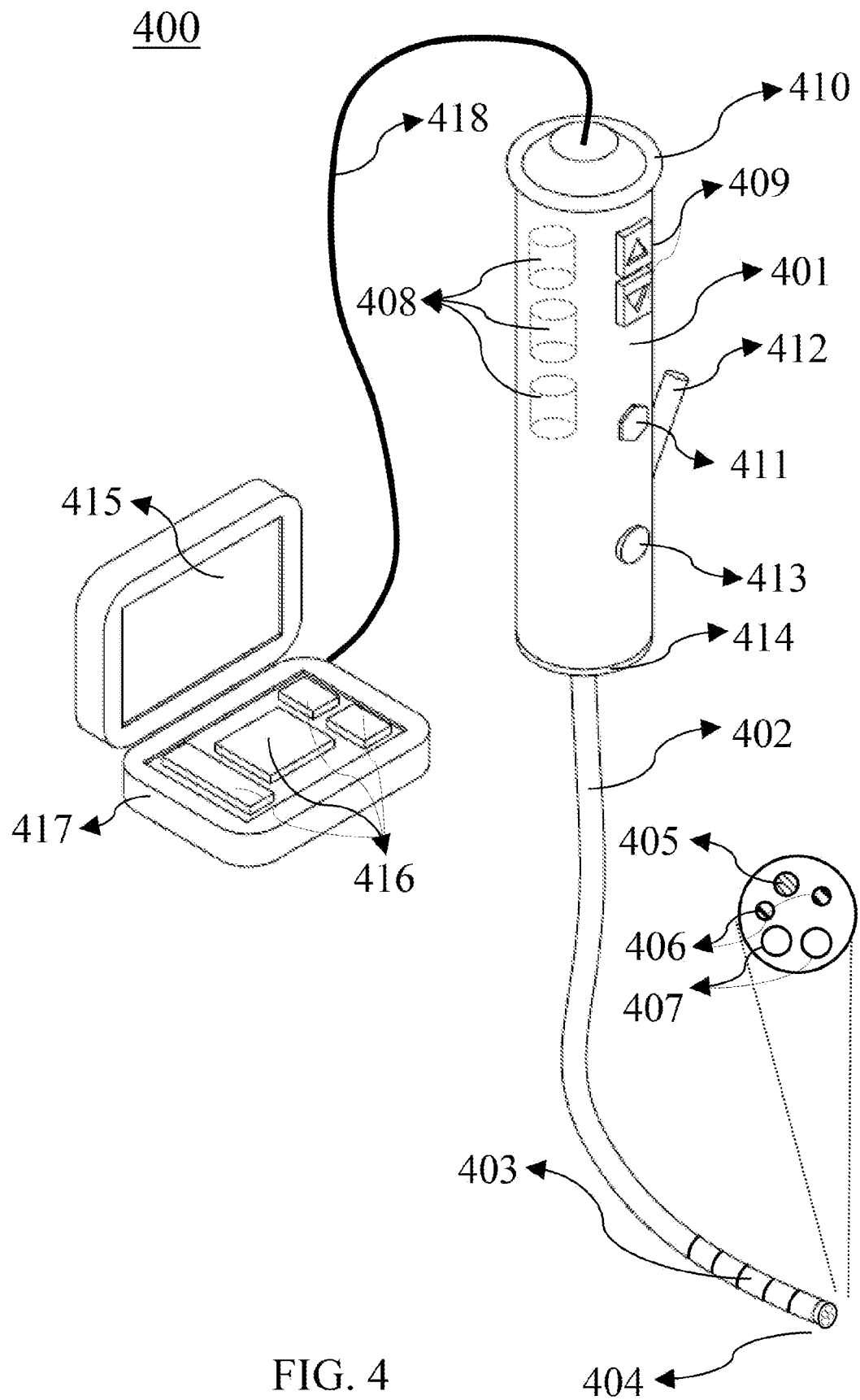
FIG. 4 illustrates an alternative embodiment of the automated intubation system according to the present invention.

FIG. 4 is an illustration of an alternative embodiment of the automated intubation system 400, which also comprises a main body 401, a flexible part 402 to connect the main body to a bending portion 403, a housing unit 404 attached to the bending portion or the flexible part. The housing unit can also support at least one imaging sensor 405, at least one guide light 406, and at least one outlet channel 407. The outlet channel 407 can be used to provide a channel in case additional devices need to be inserted such as for a biopsy, suction, and irrigation, etc. The outlet channel 407 can be used to provide a channel in case additional devices need to be inserted such as for a biopsy, suction, and irrigation, etc. The main body further comprises at least one actuation unit 408, which can be a rotational motor, linear motor, and/or a combination of both rotational and linear motor. Other types of motors would be readily apparent to a person of skill in the art. The outer surface of the main body 401 can have some or all of the following, at least one button or knob 409 to manually control the actuation, a light source 410 to indicate the power status of the automated system, a switch 411 to turn on or off the automated system, at least one port 412 for suction and a tube release switch or lever 413 to disconnect the tube from the main body and the bending portion when the tube has reached the desired position or location. The actuation unit 408 can further comprise a sliding mechanism 414.

The system further comprises a user interface 415 and a circuitry 416 arranged as a separate unit 417 outside the main body. The separate unit is connected to the main body via a cable 418. Alternatively, user interface 415, circuitry 416, and the system are connected through a wireless connection (not shown). The wireless connection can be established through Bluetooth, Wifi, Zigbee, telecommunication, NFC, or any other communication mode available at the time of implementation of the system. The wireless communication also enables the device to be controlled remotely along with the data transfer. The remotely connected processing circuitry can also control multiple actuation units at different times in multiple devices and can also provide centralized control to the hospital management and compliance department. The communication between the different units of the system can be secured by implementing technologies like SSL.

Figure 5:
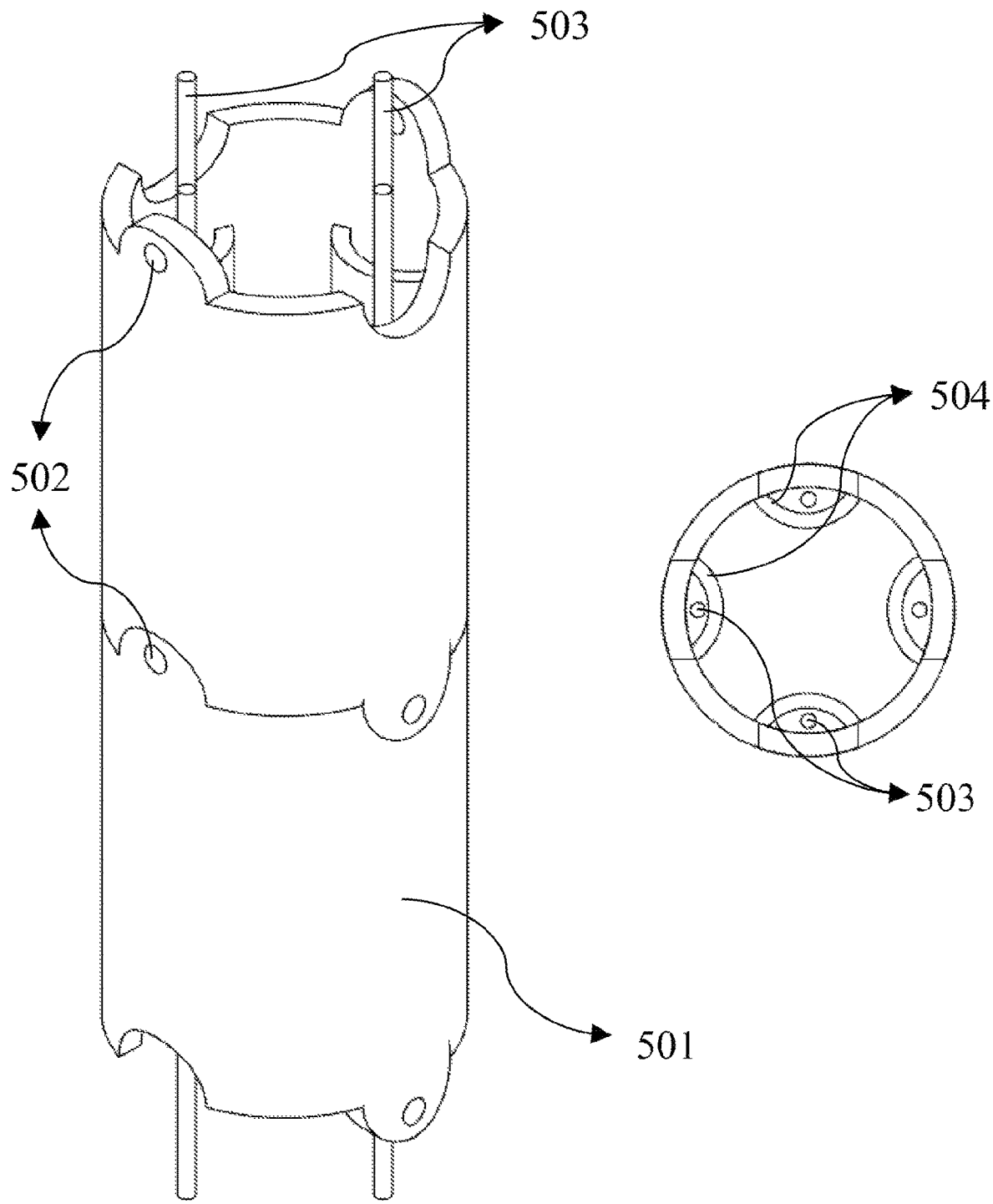
FIG. 5 illustrates a configuration of the bending portion according to the present invention.

FIG. 5 is an illustration of an exemplary embodiment of the configuration of the bending portion 203 of FIG. 2 that comprises multiple independent vertebrae 501 stacked over each other and connected by rivets 502. The vertebrae are connected in such an arrangement to allow partially and/or complete independent rotational motion of each vertebra about the rivet point. The rotational motion of each vertebra enables bending of the bending portion. The vertebrae are connected to each other via the cord(s) 503, where one end of cord(s) is connected to the actuation unit (not shown in FIG. 5) and another to the vertebra at the distal end of the bending portion. The vertebrae further comprise at least one eye loop 504 arranged on the inner side. The cord(s) from the actuation unit passes through the eye loop(s) to reach the point of connection at the distal end vertebrae. Alternatively, a mesh or a combination of the above-described configuration with mesh, or other feasible arrangements known to the person skilled in the art can be employed to achieve the same purpose.

Figure 6:
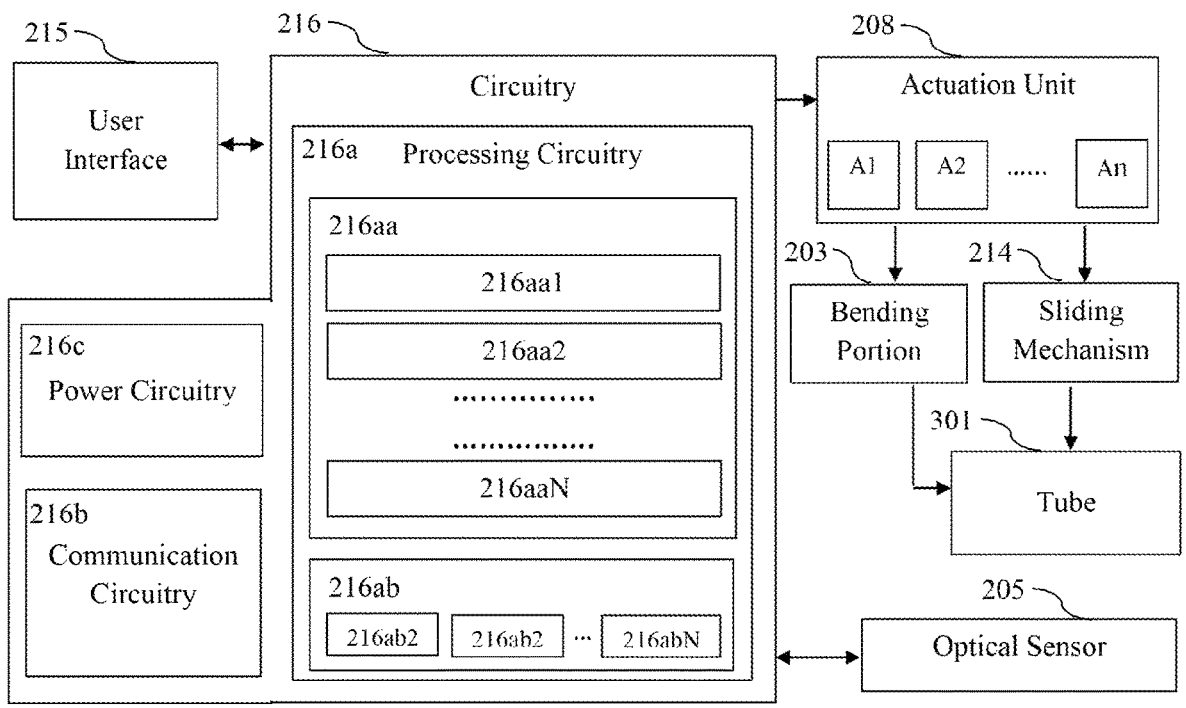
FIG. 6 illustrates an exemplary architecture of the automated intubation system according to the present invention.

FIG. 6 is an illustration of an exemplary architecture of an automated intubation system 200 which comprises a bending portion 203, an imaging sensor 205, a tube 301, at least one actuation unit 208, a user interface 215, and circuitry 216. The circuitry further comprises a processing circuitry 216a to generate control signals based on the inputs from at least one imaging sensor, a communication circuitry 216b to provide data/signal communication between different components of the system and a power circuitry 216c. The actuation unit contains a sliding mechanism 213 to provide movement to the tube in Z plane.

The processing circuitry 216a can be a single processor, logical circuit, a dedicated controller performing all the functions, or a combination of processing assisting units depending upon the functional requirement of the system. In an exemplary embodiment, the processing circuitry comprises two independent process assisting units 216aa and 216ab. The process assisting unit 216a is a computer vision software utilizing machine learning techniques and data received from the imaging sensor 205 to perform at least one function (216aa1, 216aa2 . . . 216aaN). The functions include recognition of anatomical structures and prediction of an intended path for insertion of the tube 301 based on the recognition of at least one anatomical structure. The process assisting unit and/or the processing circuitry interacts with the imaging sensor 205 to receive data during the intubation procedure and perform the aforementioned functions.

In one embodiment the recognition of anatomical structures using the imaging sensor data and the machine learning techniques include detection of respiratory structures such as tracheal opening, glottis, vocal cords, and/or bifurcation between esophagus and trachea. In addition to or substitution for detection of respiratory structures, other anatomical parts of the human body can also be detected and/or recognized.

Alternatively, the processing circuitry 216aa predicts the intended path based on the input from the imaging sensor, remotely received sample historical data from the actuation unit of multiple devices, and machine learning model. The system further stores the intended path for maintaining a log of the device operation for regulatory purposes in the memory (not shown in the system). The logs of the device can be shared with a remote device for monitoring and controlling purposes. The process assisting unit 216ab generates control signals based on the intended path predicted by process assisting unit 216aa. The control signals generated by the process assisting unit 216ab are then communicated from the processing circuitry to the actuation unit 208 via the communication circuitry 216b based upon which the actuation unit actuates at least one of the bending portion 203 and the sliding mechanism 214 to provide the three-dimensional movement to the invasive medical device. The process assisting units 216ab can also be an integrated part of the actuation unit 208 and the control signals are received by the actuation unit through wireless or wired communication circuitry. In one scenario, the processing circuitry 216aa is remotely connected through internet or wireless media with the actuation unit 208 to send the control signals. The communication circuitry can also be an integrated part of the actuation unit.

The user interface 215 is in two-way communication with the processing circuitry 106a. The user interface is preferably a display device to display data received from the imaging sensor 205 and an overlay of the recognized anatomical structures and/or the intended path received from the processing circuitry to assist an operator. Additionally, the overlaying of the intended path can also be visualized on the user interface in the form of augmented reality and/or any other form which provides effective visual guidance to the operator.

The user interface 215 can also be a touch-enabled display device that allows the operator to adjust the intended path displayed on it. The intended path displayed on the user interface can also be overridden by the operator if the operator is not satisfied with the intended path of intubation. Additionally, it can also have touch buttons pertaining to functions performed by the buttons arranged on the outer surface of the main body, such as a button to trigger manual actuation, a tube release button, and/or a system power off button. Alternatively, a user interface can be any device that can enable the operator's interaction with an automated system such as an audio input, audio output, or gesture-enabled input, or any other control scheme that can be enabled by an intelligent agent.

Figure 7:
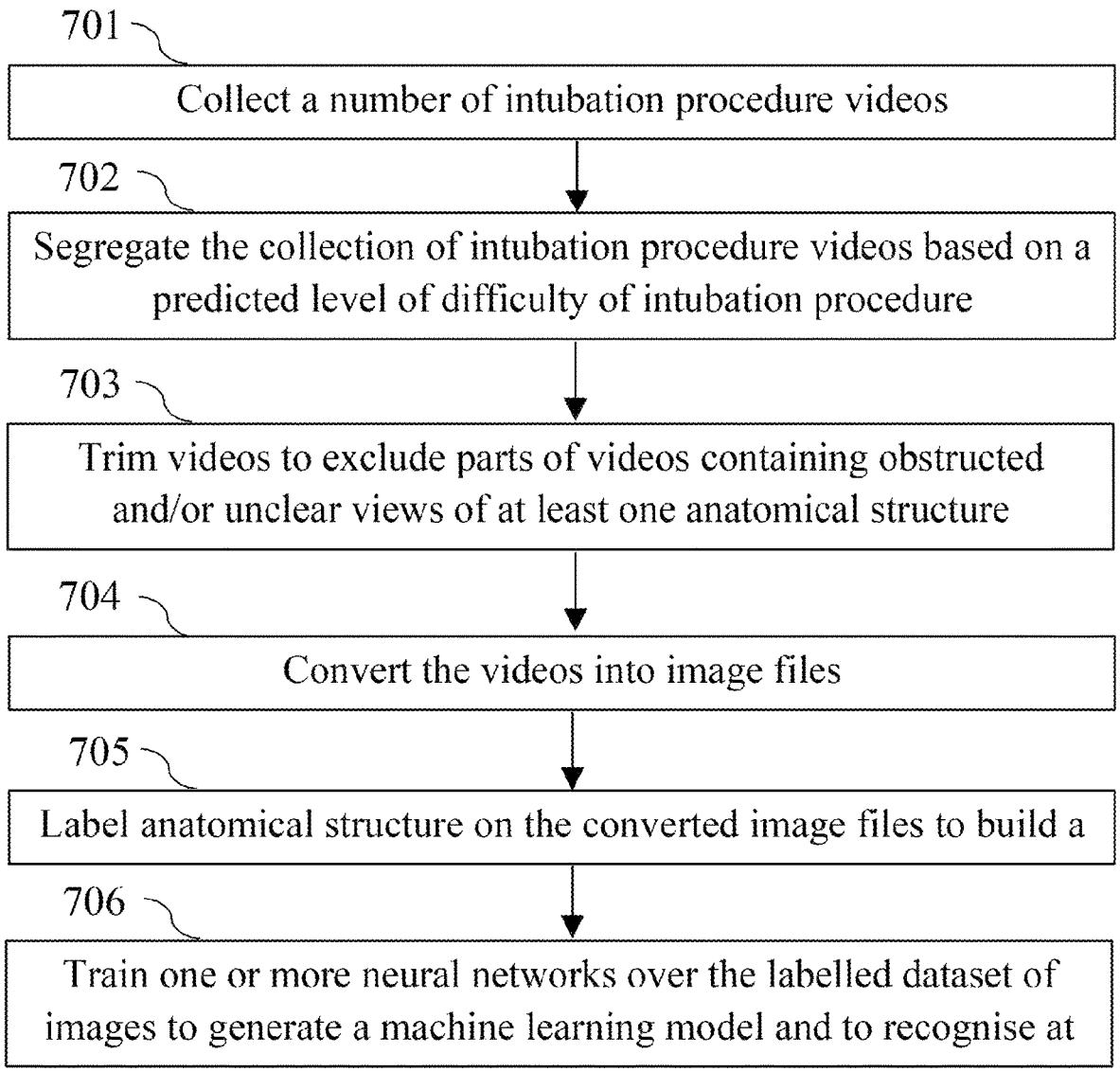
FIG. 7 illustrates a flow diagram for generating the machine learning model according to the present invention.

FIG. 7 is an illustrative flow diagram for generating a machine learning model comprising step 701 of collecting a number of intubation procedure videos from already existing video laryngoscopes and segregating the collection of intubation procedure videos based on a predicted level of difficulty of intubation procedure at step 702. The level of difficulty can be predicted either in form of conventional mallampati scores or custom intubation difficulty scales automatically using the amalgamation of computer vision models and known machine learning algorithms. The computed or predicted difficulty scores can be embedded in the metadata of the videos for easy retrieval and segregation of the video based on the computed scores. These videos can be supplemented with videos obtained from other sources, including the device described herein. There is no limitation upon the video sources used for the training videos disclosed herein.

At step 703, the segregated videos are trimmed to exclude parts of the videos containing obstructed and/or unclear views of the anatomical structure relevant to the intubation procedures. This step clears the avoidable noise in the video data before moving to the process of extensive training of machine learning models.

In step 704 the trimmed video files are converted into image files, which are then labeled with anatomical structures to build a dataset of labeled images in step 705. This labeled dataset of images acts as a training dataset to train one or more neural networks in step 706 to generate a machine learning model. The generated machine learning model is employed in or as a part of the process assisting unit 216aa (i.e. a computer vision software) executed by the processing circuitry 216a of FIG. 6 to recognize at least one anatomical structure during the intubation procedure based on the data received from the imaging sensor 205.

Figure 8:
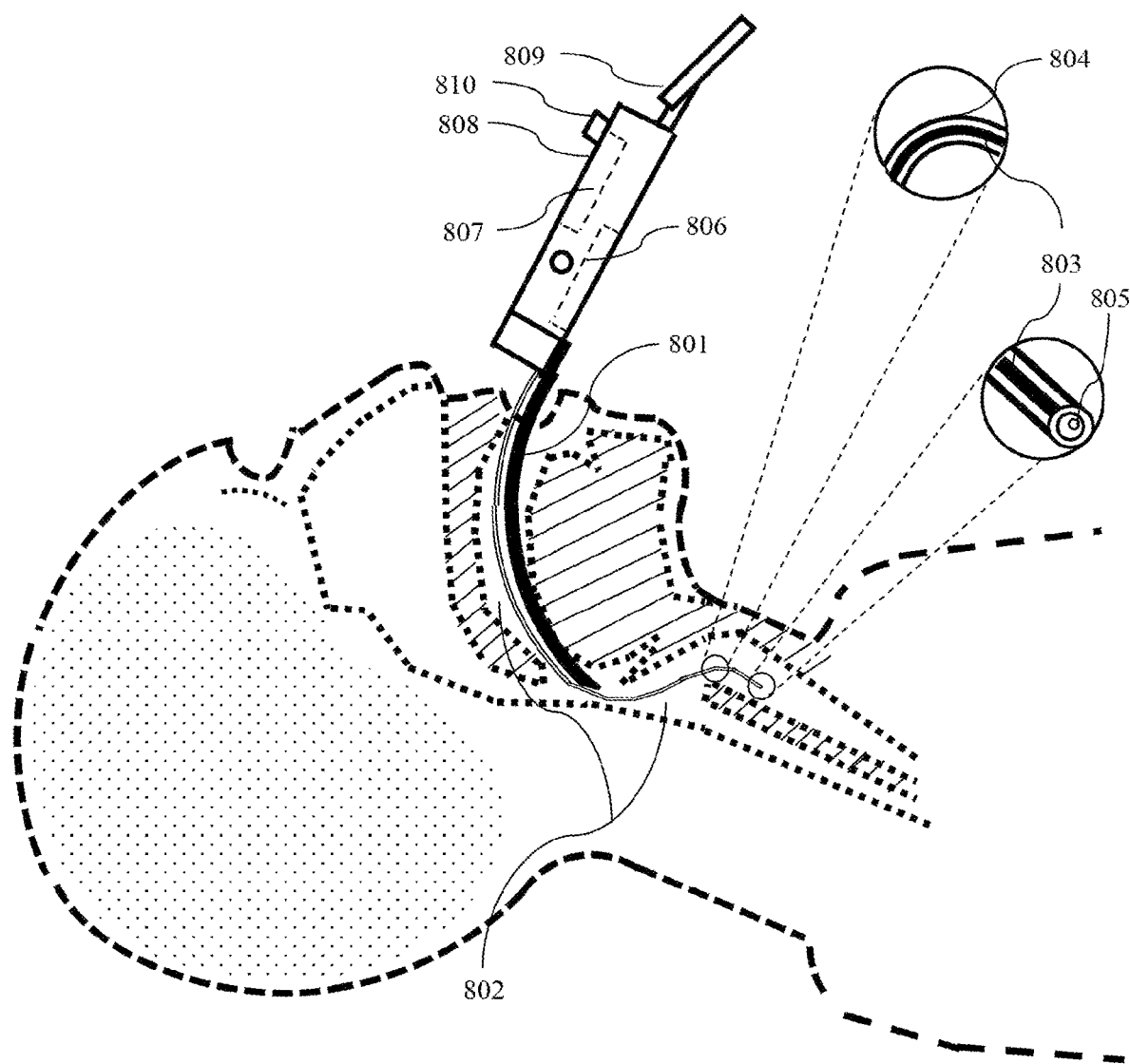
FIG. 8 illustrates the utilization of the representative automated intubation method according to the present invention.

FIG. 8 is an illustration of the utilization of the representative automated intubation method, which comprises inserting a detachable blade 801 inside an airway 802 of the patient. Adjacent to the detachable blade, a bending portion 803 and a tube 804 arranged longitudinally on the bending portion is inserted into the airway of the patient. The method further involves collecting airway data from at least one imaging sensor 805 arranged on the bending portion. The collected airway data is then communicated to at least one processing circuitry 806, which utilizes a machine learning model and airway data to recognize at least one anatomical structure and predict at least one intended path for insertion of the tube. The intended path is then used by the processing circuitry to generate and communicate control signals to at least one actuation unit 807 to actuate the three-dimensional movement of the tube.

Particularly, the detachable blade 801, the bending portion 803, and the tube are inserted by introducing the main body 808 in the vicinity of the patient's mouth, as the detachable blade, the bending portion, and the tube are directly or indirectly connected to the main body. Also, the processing circuitry 806 and the actuation unit 807 is preferably located within the main body.

The three-dimensional movement of the tube 804 arranged on the bending portion 803 includes bending movement of the tube in X and Y plane guided by the two-dimensional movement of the bending portion 803, and movement of the tube in Z plane by a sliding mechanism (not shown in FIG. 8) of the actuation unit 807. The actuation of the bending portion is enabled by the actuation unit connected to the bending portion via cord(s) (not shown in FIG. 8). The method also comprises displaying data communicated from the imaging sensor(s) 805 on a user interface 809, and overlaying of the recognized anatomical structures and the intended path of insertion of the tube on the user interface.

The position of the distal end of the tube can be confirmed by standard methods of clinical care such as but not limited to capnometry, X-rays, and ultrasound. These methods can be incorporated into the device directly, or incorporated to provide indirect support for such methods. For example, with regard to capnometry, the presence of $CO_2$ levels within the air can confirm accurate placement of the tube within the patient. This qualitative or quantitative confirmation can be provided by sensors directly placed on or within the device such as a $CO_2$ monitor, or via more indirect methods such as a color-changing PH sensitive strip placed within view of the imaging sensor to provide confirmation of the correct $CO_2$ levels. Similarly, the ultrasound transmitters and receivers can be incorporated into the device that can confirm that the distal end of the tube is placed correctly. The techniques discussed above are just a few of the many clinical approaches to confirm the correct placement of the intubation tube that would be obvious to a person of skill in the art.

Upon reaching the desired position or location inside the airway of the patient, the tube is set to release from the main body 808 and the bending portion 803 using a tube release switch or lever 810 located on the outer surface of the main body. Alternatively, a touch button (not shown in FIG. 8) can also be provided on the user interface 809 to release or disconnect the tube.

Figure 9:
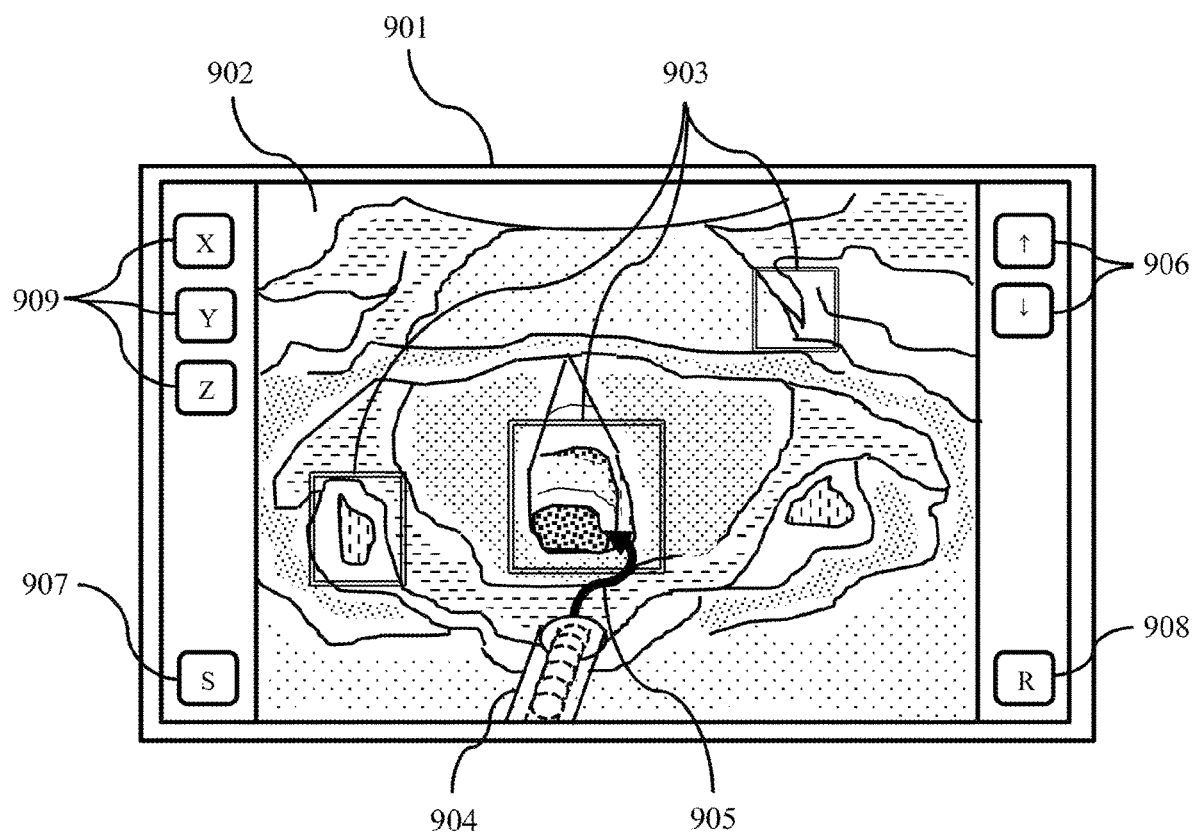
FIG. 9 illustrates the utilization of the user interface according to the present invention.

FIG. 9 is an illustration of the utilization of the user interface 901 which comprises a display screen 902 to display the data received from at least one imaging sensor. The display screen further displays an overlay of at least one recognized anatomical structure 903 and the intended path of insertion 905 of the tube 904. An operator can also manually adjust the intended path of insertion 905 of the tube 904 displayed on the user interface. Alternatively, the overlay of the tube, the bending portion, recognized anatomical structure 903, and intended path of insertion 905 is displayed on the user interface as augmented reality, virtual reality, or other forms of overlaying known to the person skilled in the art to provide effective visual guidance to an operator. The overlay of recognized anatomical structures can also include annotations or labels for quick identification of structures by an operator during the procedure.

Additionally, the display screen 902 of the user interface 901 can comprise a pair of up and down touch buttons 906 to manually control the actuation and/or override the automated actuation if required, a system power on/off touch button 907, and a tube release touch button 908.

In one embodiment, the pair of up and down touch button 906 can be used to selectively control manual actuation in selected working planes X, Y, or Z. The touch button 909 provided on the display screen can be used to select a plane of working before providing input via touch buttons 906. It should be understood that although the touch buttons are depicted in FIG. 9 to be arranged outside the boundary of visual data received from the imaging sensor, the arrangement of the touch buttons can be changed to provide the best possible visual representation to the operator.

Although the present invention has been explained in the context of assistance to surgery, insertion, or implantation, the present invention can also be exercised to realize the educational or academic use such as in training and demonstrations.

No language in the specification should be construed as indicating any non-claimed element as essential to the practice of the invention.

It will be apparent to those skilled in the art that various modifications and variations can be made to the present invention without departing from the spirit and scope of the invention. There is no intention to limit the invention to the specific form or forms enclosed. On the contrary, the intention is to cover all modifications, alternative constructions, and equivalents falling within the spirit and scope of the invention, as defined in the appended claims. Thus, it is intended that the present invention cover the modifications

What is claimed is:

1. An automated intubation system, comprising:
   a tube;
   a flexible part disposed longitudinally within the tube;
   a bending portion forming at least a part of a distal end of the flexible part;
   a housing unit disposed at a distal end of the bending portion and comprised of at least one imaging sensor;
   a processing circuitry predicting at least one intended path for insertion of the tube and generating control signals;
   a user interface displaying the at least one intended path and also allowing at least one of: selection of the at least one intended path, or modification of the at least one intended path; and
   at least one actuation unit receiving the control signals for actuating three-dimensional movement of the tube along the selected or modified at least one intended path,
   wherein the at least one intended path is configured to be predicted based on at least one anatomical structure recognized using data received from the at least one imaging sensor, historical data received from the at least one actuation unit, and a machine learning model
   wherein the machine learning model is configured to be generated by:
      collecting a plurality of intubation procedure videos;
      segregating the plurality of intubation procedure videos based upon a predicted level of difficulty of an intubation procedure of each of the plurality of intubation procedure videos;
      trimming the segregated intubation procedure videos to exclude parts of videos containing unobstructed and/or unclear views of the at least one anatomical structure;
      converting the trimmed videos into at least one image file;
      assigning a label indicating the at least one anatomical structure to the at least one converted image file to build a labelled dataset of a plurality of images; and
      training one or more neural networks using the labelled dataset of the plurality of images.

2. The automated intubation system of claim 1, wherein the at least one actuation unit receives the control signals from the processing circuitry via at least one communication circuitry.

3. The automated intubation system of claim 1, wherein the at least one actuation unit is connected to the bending portion to actuate a bending movement of the tube in an X plane and a Y plane.

4. The automated intubation system of claim 1, wherein the at least one actuation unit comprises a sliding mechanism to actuate a sliding movement of the tube in a Z plane.

5. The automated intubation system of claim 1, wherein the automated intubation system further comprises at least one button to trigger the at least one actuation unit, a switch to release the tube, and at least one port to provide a channel for at least one of instrumentation, suction, or irrigation.

6. The automated intubation system of claim 1, wherein the processing circuitry is configured to utilize the machine learning model to recognize the at least one anatomical structure and to subsequently predict the at least one intended path based on the data received from the at least one imaging sensor and the historical data received from the at least one actuation unit, and to generate the control signals based on the selected or modified at least one intended path.

7. The automated intubation system of claim 1, wherein the automated intubation system is connected to a network and is configured to be controlled by a remote operator.

8. The automated intubation system of claim 1, wherein the user interface is configured to display an overlay of the at least one anatomical structure, and an overlay of the at least one intended path over the data received from the imaging sensor.

9. The automated intubation system of claim 1, wherein the selection or modification of the at least one intended path displayed on the user interface is configured to be performed by an operator.

10. The automated intubation system of claim 1, wherein the actuation of the three-dimensional movement of the tube along the selected or modified intended path is configured to be overridden by an operator via the user interface when the operator is not satisfied with the at least one intended path.

11. The automated intubation system of claim 1, further comprising:
    a main body; and
    a detachable blade connected to the main body via a disposable and/or a reusable sleeve, wherein the flexible part is connected to the main body.

12. The automated intubation system of claim 1, wherein the housing unit further comprises at least one of a guide light and an outlet channel.

13. A method of automatically intubating a patient, the method comprising:
    inserting a bending portion of a flexible part disposed longitudinally within a tube inside an upper airway of the patient;
    collecting data from at least one imaging sensor disposed within the bending portion;
    communicating collected data to a processing circuitry;
    predicting at least one intended path for insertion of the tube using the processing circuitry;
    displaying the at least one intended path via a user interface to an operator;
    receiving at least one of selection of the at least one intended path, or modification of the at least one intended path from the operator via the user interface;
    generating control signals based on the selected or modified at least one intended path using the processing circuitry; and
    communicating the generated control signals to at least one actuation unit for actuating a three-dimensional movement of the tube along the selected or modified at least one intended path, wherein the at least one intended path is predicted based on at least one anatomical structure recognized using data received from the at least one imaging sensor, historical data received from the at least one actuation unit, and a machine learning model
    wherein the machine learning model is generated by:
       collecting a plurality of intubation procedure videos;
       segregating the plurality of intubation procedure videos based upon a predicted level of difficulty of an intubation procedure of each of the plurality of intubation procedure videos;
       trimming the segregated intubation procedure videos to exclude parts of videos containing unobstructed and/or unclear views of the at least one anatomical structure;
       converting the trimmed videos into at least one image file;

assigning a label indicating the at least one anatomical structure to the at least one converted image file to build a labelled dataset of a plurality of images; and training one or more neural networks using the labelled dataset of the plurality of images.

14. The method of claim 13, wherein communicating the control signals comprises communicating X directional control signals and Y directional control signals to the at least one actuation unit for actuating a bending movement of the tube in an X plane and a Y plane via the bending portion.

15. The method of claim 13, wherein communicating the control signals comprise communicating Z directional control signals to the at least one actuation unit for actuating a sliding movement of the tube in a Z plane via a sliding mechanism.

16. The method of claim 13, wherein the recognition of the at least one anatomical structure and the subsequent prediction of the at least one intended path is performed using the machine learning model and based on the data collected from the at least one imaging sensor.

17. The method of claim 13, wherein the user interface displays an overlay of the at least one anatomical structure, and an overlay of the at least one intended path over the data received from the at least one imaging sensor.

18. The method of claim 13, wherein the selection or modification of the at least one intended path displayed on the user interface is performed by the operator.

* * * * *